United States Patent [19]

Imamura et al.

[11] Patent Number: 5,148,233
[45] Date of Patent: Sep. 15, 1992

[54] OPTICAL ATTENUATOR AND OPTICAL POWER METER CALIBRATION SYSTEMS WITH OPTICAL-PULSE CONVERSION AND AVERAGING

[75] Inventors: Takayuki Imamura, Kawasaki; Yuji Ohuchi, Atsugi, both of Japan

[73] Assignee: Anritsu Corporation, Tokyo, Japan

[21] Appl. No.: 603,884

[22] Filed: Oct. 25, 1990

[30] Foreign Application Priority Data

Oct. 31, 1989 [JP] Japan .................. 1-284106
Mar. 30, 1990 [JP] Japan .................... 2-86975

[51] Int. Cl.$^5$ .............................................. G01J 1/00
[52] U.S. Cl. .................... 356/243; 356/235; 250/252.1
[58] Field of Search ............... 356/432, 433, 434, 235, 356/243; 350/269, 272, 274; 250/252.1 A; 359/235

[56] References Cited

U.S. PATENT DOCUMENTS

| | | | |
|---|---|---|---|
| 2,166,947 | 7/1939 | Fayerweather | 350/272 |
| 3,435,213 | 3/1969 | Colbow et al. | 350/274 |
| 4,281,897 | 8/1981 | Fletcher | 350/274 |
| 4,413,179 | 11/1983 | Matsuoka et al. | 350/269 |

FOREIGN PATENT DOCUMENTS

| | | | |
|---|---|---|---|
| 648167 | 9/1962 | Canada | 356/243 |
| 64-35323 | 2/1989 | Japan . | |

OTHER PUBLICATIONS

C. L. Sanders, Accurate Measurements of and Corrections for Nonlinearities–in Radiometers, Sep. 1972, 437–453, Journal of Research of the National Bureau of Standards–A. Physics and Chemistry, vol. 76A, No. 5.
O. C. Jones and F. J. J. Clarke, A New Photometric Technique Using a Variable Shutter Device, Nature, vol. 191, Sep. 23, 1961, p. 1290.
H. Kunz, Representation of the Temperature Scale Above 1337.58K with Photoelectric Direct Current Pyrometers, Metrologia, vol. 5, No. 3, 1969, pp. 88–102.
H. J. Jung, Kompesation von Nichtlinearitaten bei photoelektrischen Strahlungsmessungen, Z. Angew. Physik, vol. 31, 1971, pp. 170–176.

*Primary Examiner*—Richard A. Rosenberger
*Attorney, Agent, or Firm*—Frishauf, Holtz, Goodman & Woodward

[57] ABSTRACT

The invention is designed to calibrate a low-level optical power by a substitution method using a pulse generating section in which a light-shielding disk having a sectorial opening, as a component capable of accurate optical attenuation, is rotated in a light beam to generate an intermittent pulse signal having a duty ratio corresponding to the size of the opening, and the pulse signal is averaged to obtain an optical attenuation equal to the duty ratio. More specifically, while an object to be calibrated is set in a given standard state, a first pulse train having a duty ratio $d1 = Tw_1/Tf_1$ is input to the object, and an average optical power value A of an output from the object is measured and stored. Subsequently, a second pulse train having a duty ratio $d2 = Tw_2/Tf_2$ is input to the object, and the object is adjusted such that an average optical power value of an output from the object becomes the value A. Proper calibration can be performed by assigning the optical attenuation of the adjusted object to $d1/d2$.

23 Claims, 13 Drawing Sheets

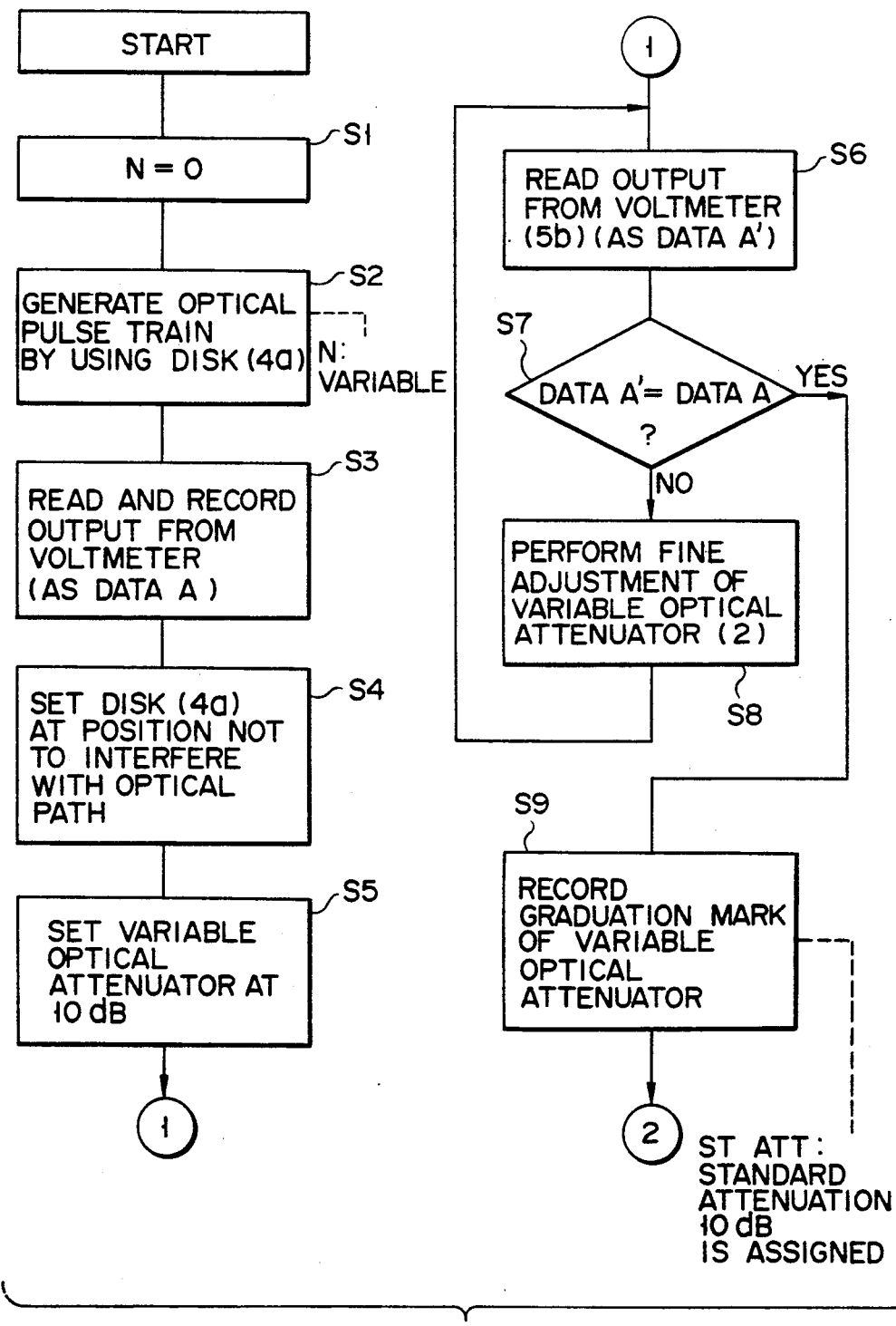
FIG. 2C-i

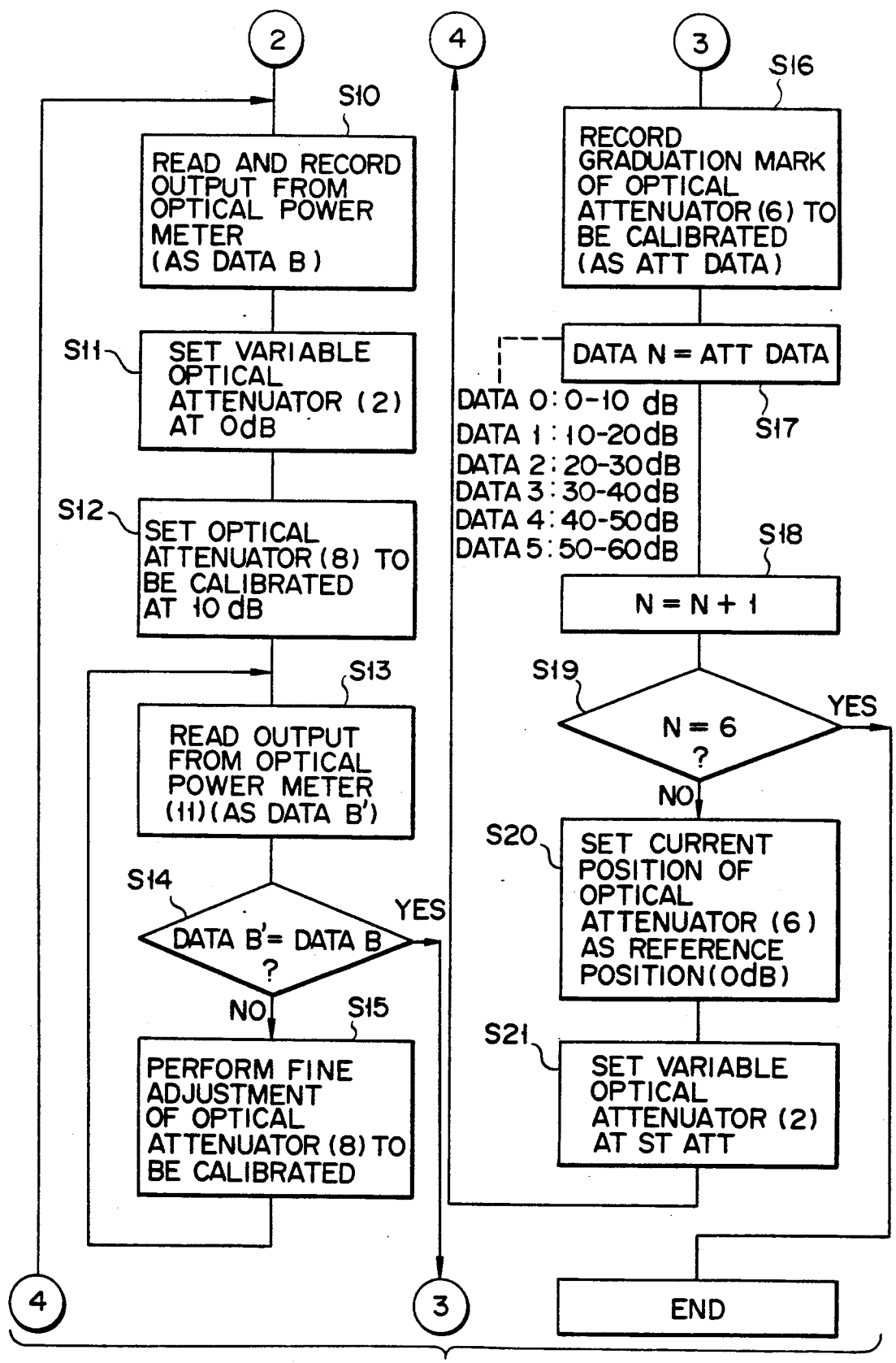
FIG. 2C-ii

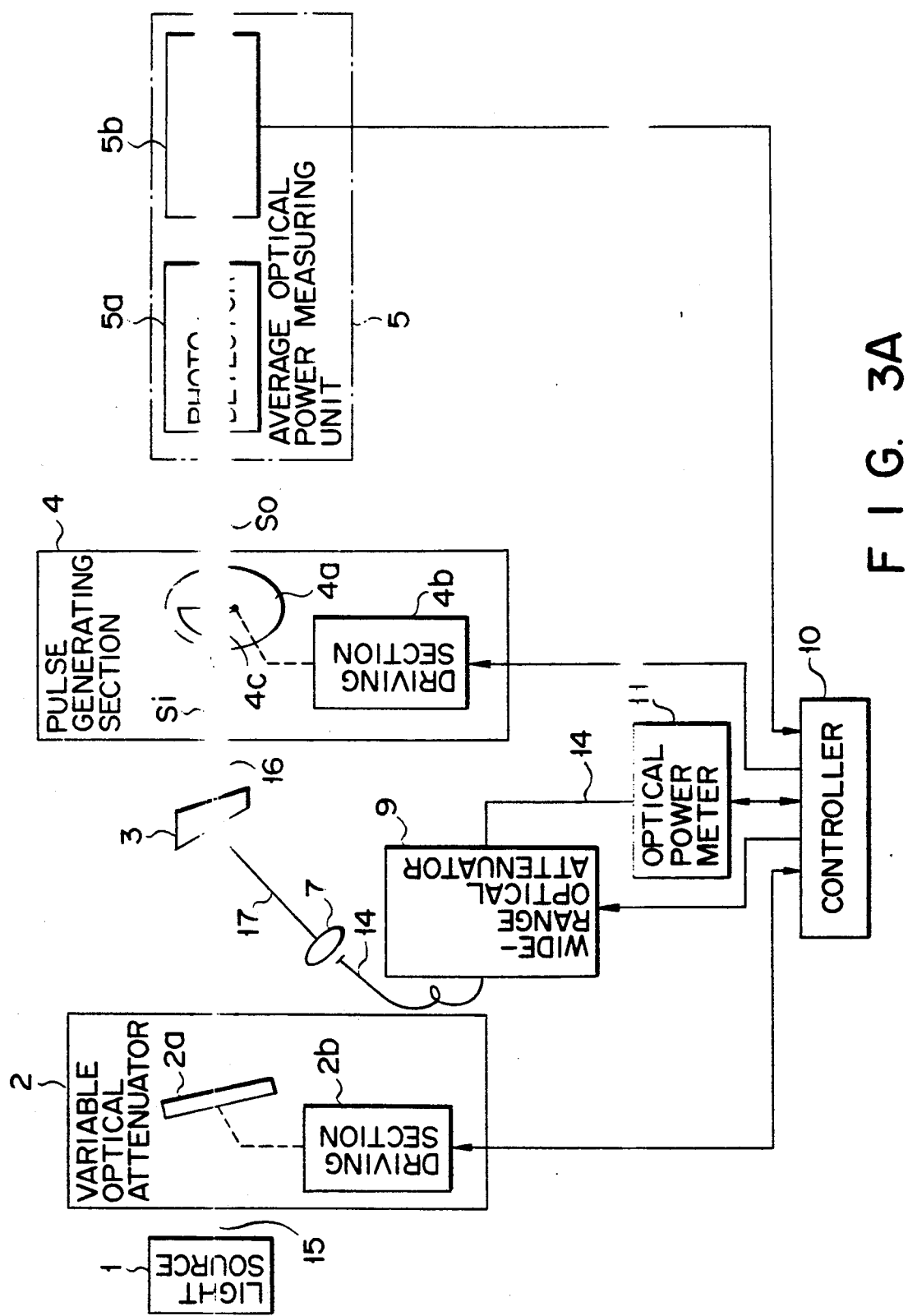
F I G. 3A

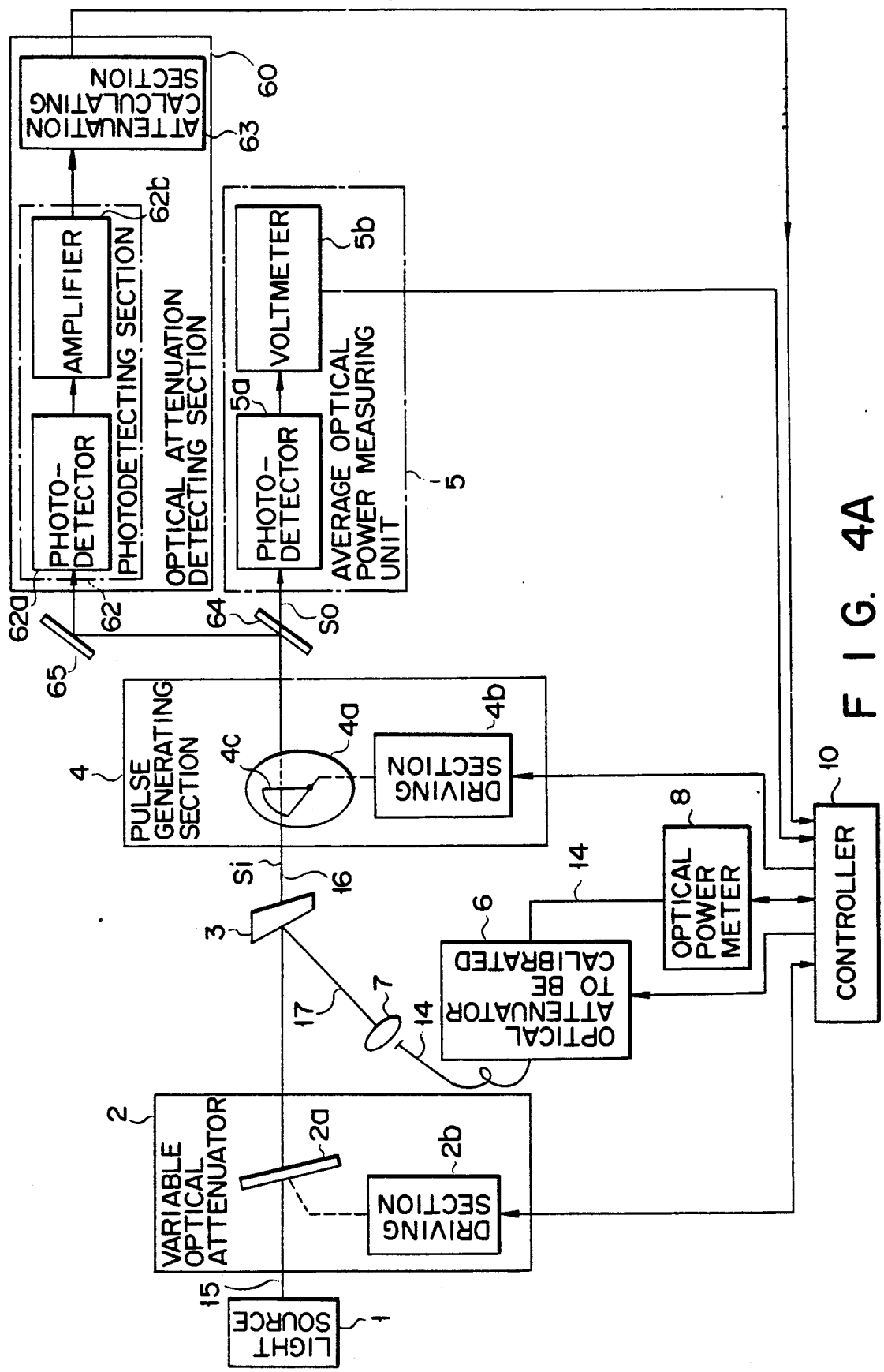
F I G. 4A

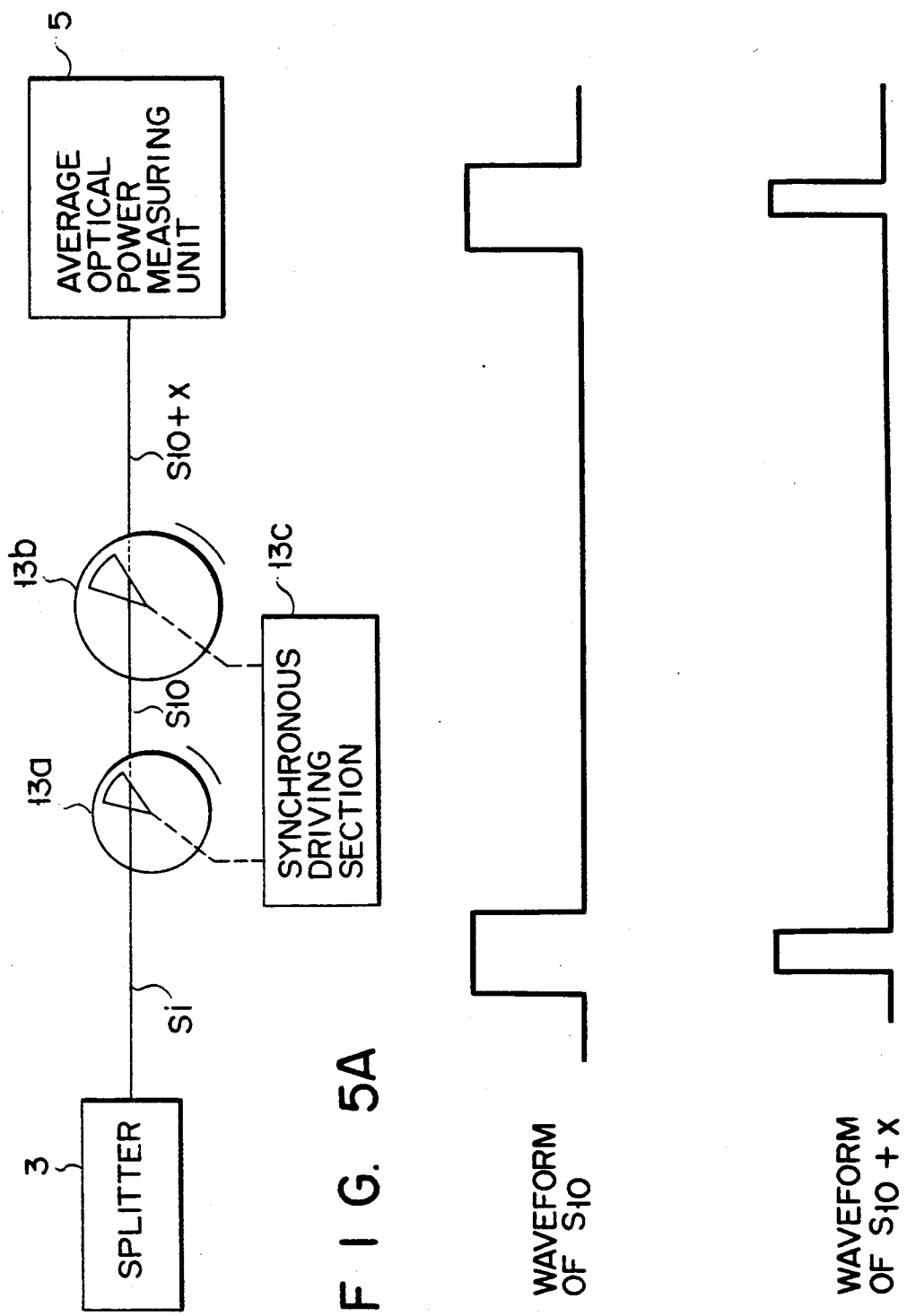

OPTICAL ATTENUATOR AND OPTICAL POWER METER CALIBRATION SYSTEMS WITH OPTICAL-PULSE CONVERSION AND AVERAGING

BACKGROUND OF THE INVENTION

1. Field of the Invention

The present invention relates to optical attenuator and optical power meter calibration systems with an optical-pulse conversion and averaging In addition, the present invention relates to an optical attenuation calibration method and apparatus, and an optical power meter calibration apparatus for calibrating the optical attenuation or linearity of an object to be calibrated and, more particularly, to an optical calibration apparatus mainly used to calibrate the optical attenuation of an optical component such as an optical attenuator and to calibrate the linearity of an optical power meter Furthermore, the present invention relates to an apparatus capable of setting an accurate optical attenuation in calibration requiring high-precision measurement and to an optical attenuation calibration method and apparatus, and an optical power meter calibration apparatus for performing calibration by using the set optical attenuation as a standard optical attenuation.

2. Description of the Related Art

There is a great demand for accurate measurement of a low-level optical power. Such measurement has been performed in the following manner.

a) An optical absolute power for calibration is calibrated at a high level point The optical absolute power is then attenuated by an accurate optical attenuator having no errors. A low-level optical power is calibrated and measured by comparison with this optical absolute power. However, an accurate optical attenuator having no errors which can be used in this method is not available. Therefore, satisfactory accuracy cannot be obtained.

b) If a low-level optical power is to be directly measured, a large error is inevitably caused by the influences of the linearity of a photodetector.

Currently, no calibration service for optical attenuation is available from any public institution in any country.

More specifically, in a conventional method, measurement of the optical attenuation of an optical attenuator is generally performed by an arrangement shown in FIG. 10A. In the arrangement shown in FIG. 10A, if an optical power value indicated by an indicator 44 when light from a light source 41 is converted into an electrical signal by a photodetector 43 without causing it to pass through using an optical attenuator 42 is represented by $P_0(W)$ as indicated by a dotted line, and an optical power value indicated by the indicator 44 when light passes through the optical attenuator 42 is represented by $P_1(W)$ as indicated by a solid line, an optical attenuation A can be given by the following equation:

$$A = 10 \times \log(P_0/P_1) \quad (unit: dB)$$

In this case, since the photodetector 43 detects different optical powers, the linearity of the photodetector 43 causes measurement errors. If a photodiode sensor is used as the photodetector 43, the linearity is influenced by the diode characteristics. If a thermoelectric conversion type sensor (a Peltier effect element, thermopile, or the like) is used, the linearity is influenced by the thermoelectric conversion characteristics, and heat radiation and convection.

If such linearity of the photodetector 43 is calibrated in advance, correction can be performed. For this purpose, however, a calibration standard having an accurate optical attenuation is required.

Assume that a standard optical attenuator 45 having an accurate optical attenuation is available. In this case, if the attenuator 45 is inserted between the optical attenuator 42 and the photodetector 43, as indicated by FIG. 10B, so as to perform measurement (or calibration) by a serial substitution method, since the photodetector 43 receives substantially the same optical power, measurement is substantially free from the influences of the linearity.

The serial substitution method will be briefly described below with standard to FIG. 10B. If, for example, a nominal value of 10 dB of an optical attenuator 42 is to be calibrated, the standard optical attenuator 45 having an attenuation which can be accurately changed to 0 dB and 10 dB is inserted in series. The attenuation of the standard optical attenuator 45 is set to be 10 dB, and an optical signal from the light source is measured through the attenuator 45 without the optical attenuator 42, as indicated by the dotted line. At this time, a value $P_2(W)$ indicated by the indicator 44 is read. Then the attenuation of the standard optical attenuator 45 is set to be 0 dB, and the optical attenuator 42 is inserted in series, as indicated by the solid line. If the value indicated by the indicator 44 at this time is $P_3(W)$, an accurate attenuation of the optical attenuator 42 is given by $[10 + 10 \times \log(P_2/P_3)] dB$.

According to this calibration technique, the standard optical attenuator is indispensable. Currently, however, such a standard optical attenuator is very difficult to obtain.

A method of setting a standard optical attenuation in calibration is disclosed in Japanese Patent Application No. 62-193068 (Published Unexamined Japanese Patent Application No. 64-35323) assigned to the same assignee as that of the present application. An outline of this method will be described below with standard to FIG. 11. Referring to FIG. 11, first and second light amount adjusting units 53 and 54 are adjusted such that the optical powers of first and second light from light sources 51 and 52 for generating light beams having wavelengths close to each other become equal to each other. Assume that, after this operation, a value of power received by an optical power meter 58 under calibration when one of first and second switches 55 and 56 is turned on is represented by $P_A(W)$, and a value of power received by the optical power meter 58, which received synthesized light from a light synthesizing section 57 when both the switches 55 and 56 are turned on, is represented by $P_{AB}(W)$. In this case, the ratio of the optical powers $(P_{AB}/P_A)$ is 3.01013 dB $(P_{AB}/P_A=2)$. The linearity of the power meter 58 is calibrated by a $2^N$ method disclosed in Published Unexamined Japanese Patent Application No. 64-35323 by using the ratio of the optical powers as a standard optical attenuation. In this case, the $2^N$ method is a method of measuring linearity in a level range of $2^N$ (or $2^{-N}$) by sequentially accumulating 2 times (or ½ times) a light amount (by means of addition of equal light amount) in measurement steps.

In the case shown in FIG. 11, as the first and second light sources 51 and 52, coherent light sources must be selected, which do not interfere with each other and have a wavelength gap enough to be free from the influences of the wavelength characteristics of the optical power meter 58. In the technique disclosed in Published Unexamined Japanese Patent Application No. 64-35323, since formation of optical attenuations other than 3.0103 dB is not proposed, in order to perform calibration in a wide range, complicated control such as the $2^N$ method is required.

Note that prior arts associated with the present invention include an experimental apparatus wherein an average level of transmitted light is changed in accordance with a time in which a window formed in a rotating sector crosses the transmitted light (Journal of Research of the National Bureau of Standards, Vol. 76A, No. 5 September - October 1972, pp 437-453). However, no prior arts associated with a calibration apparatus and method of the present invention (to be described below) have been disclosed.

As described above, in the conventional methods, in order to realize a calibration apparatus for an optical attenuation, an optical attenuator having an accurate optical attenuation as a standard is required. However, such an attenuator is not currently available. Therefore, a complicated arrangement is required to calibrate the optical attenuation or insertion loss of an optical component such as an optical attenuator or to calibrate an optical power meter. In addition, the conventional methods require sophisticated techniques.

SUMMARY OF THE INVENTION

It is, therefore, an object of the present invention to provide an optical attenuation calibration method and apparatus, and an optical power meter calibration apparatus, which can set a standard optical attenuation and can perform high-precision calibration on the basis of the standard optical attenuation.

In order to achieve the above object, according to the present invention, firstly, the following technique is used. If an optical pulse train obtained by sequentially turning on and off light is received and integrated, its average optical power is varied in accordance with the duty ratio of the optical pulse. More specifically, an arrangement for calibration of an optical attenuation is constituted by a combination of a pulse generating means capable of setting an optical attenuation as a calibration standard by changing the duty ratio of an optical pulse and a photodetecting means including a sensor for detecting the characteristics of the optical pulse. In order to set an optical attenuation, the photodetecting means for detecting an optical pulse from the pulse generating means, detecting the duty ratio of the optical pulse, and calculating an optical attenuation from the duty ratio is used. Alternatively, a combination of an average optical power measuring unit for outputting the average power of the optical pulse and the photodetecting means is used to constitute an arrangement which can contribute to calibration of an optical attenuation.

Secondly, a standard optical attenuation is set by the mechanical structure of the pulse generating means. More specifically, by rotating a disk having an opening with a proper angle, an average optical attenuation is substituted by a geometrical dimension.

Thirdly, a calibration method and apparatus using a serial substitution method is employed.

The respective means in calibration based on the serial substitution method will be described below. A light source, a pulse generating means, and an average optical power measuring unit are connected to each other through one optical path. The pulse generating means is designed to switch and output a first optical pulse train having a duty ratio Tw/Tf of 1/10 and a second optical pulse train having a duty ratio of unity (a continuous light for Tw=Tf=1), provided the target calibration value of an object to be calibrated is 10 (dB). The average optical power measuring unit is designed to output an average optical power value Pm when the first optical pulse train is output and to output an average optical power value Pn when the second optical pulse train is output.

In this case, $10 \times \log(Pn/Pm) = 10$ dB.

Subsequently, the object to be calibrated is set on the optical path before or after the pulse generating means. While the pulse generating means outputs the second optical pulse train (duty ratio Tw/Tf=1), the position of the object is changed to set an average power output from the average power measuring unit to be the value Pm. The position where the average power becomes the value Pm is set to be an optical attenuation of 10 dB.

The present invention can be used as a standard optical attenuator. In addition, if the substitution method is used, the present invention can be used to calibrate the attenuation of an object to be calibrated with high precision regardless of the linearity of a detector.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 2C-i and 2C-ii are flow charts for explaining a first operation;

FIG. 3A is a block diagram showing an arrangement of the second embodiment of the present invention;

FIG. 4A is a block diagram showing an arrangement of the third embodiment of the present invention;

FIGS. 5A, 5B, and 5C are views for explaining an arrangement and an operation of a modification of the pulse generating section in the first to third embodiments of the present invention;

DETAILED DESCRIPTION OF THE PREFERRED EMBODIMENTS

Figure 1:
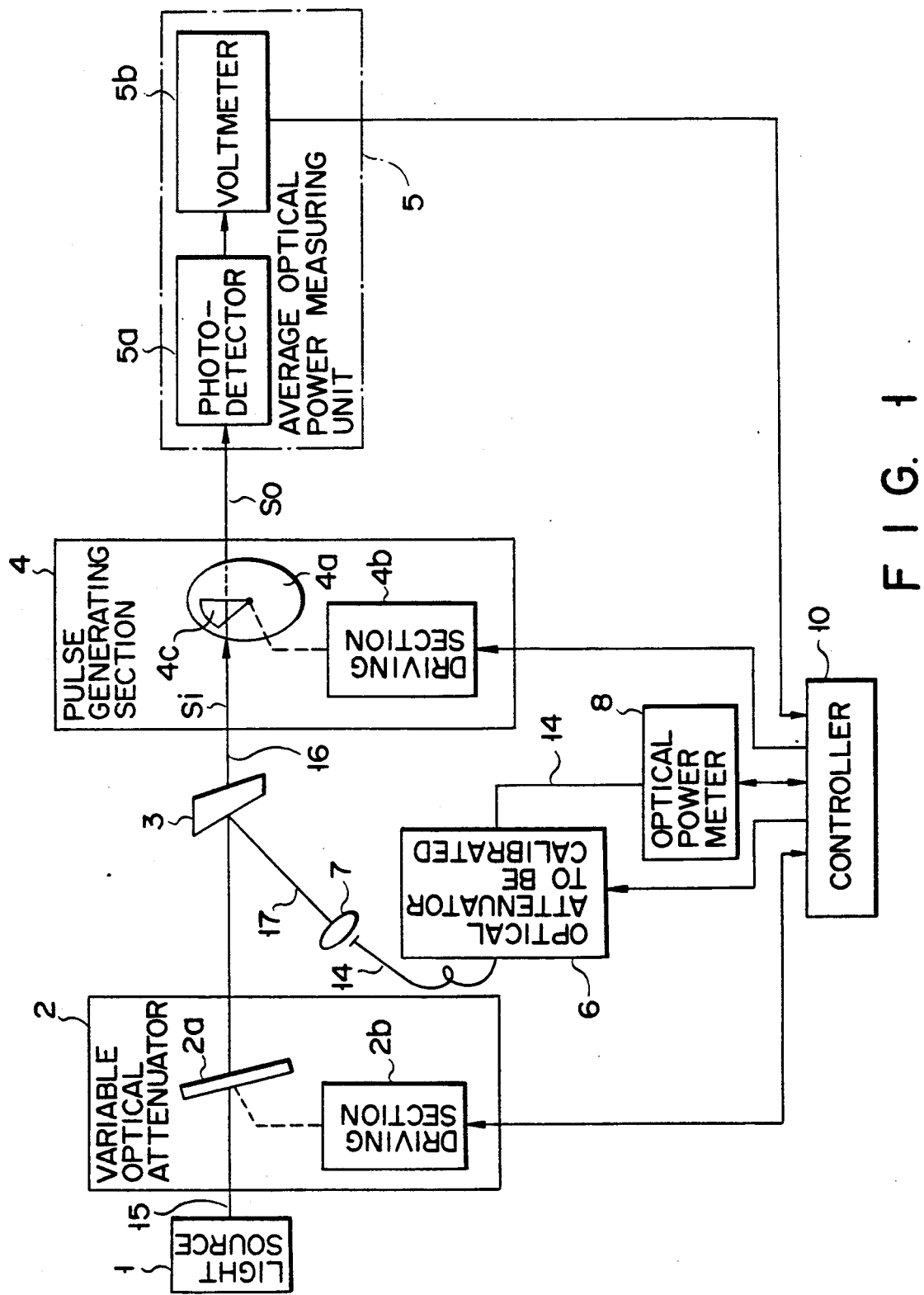
FIG. 1 is a block diagram showing an arrangement of the first embodiment of the present invention.

Reference will now be made in detail to the presently preferred embodiments of the invention as illustrated in the accompanying drawings, in which like reference characters designate like or corresponding parts throughout the several drawings.

FIRST EMBODIMENT

FIG. 1 shows an arrangement of an embodiment which is applied to an optical attenuation calibration metho and apparatus according to the present invention.

In the arrangement shown in FIG. 1, a variable optical attenuator 2 is calibrated by a light source 1, a pulse generating section 4, and an average optical power measuring unit 5, and an optical attenuator 6 to be calibrated as a final calibration target is then calibrated by the calibrated variable optical attenuator 2, an optical beam splitter 3, and an optical power meter 8.

An object to be calibrated includes both the variable optical attenuator 2 associated with intermediate calibration and the optical attenuator 6 to be calibrated which is associated with final calibration.

In general, calibration of an optical attenuation includes the following two cases: a case wherein the nominal value of the optical attenuation of an object to be calibrated is known, and calibration is performed to accurately correct the nominal value; and a case wherein the optical attenuation of an object to be calibrated, whose nominal value is unknown, is measured and assigned to a reading. This embodiment will be described with reference to the latter case.

The main components of the embodiment shown in FIG. 1 will be described below.

In this embodiment, a laser diode is used as the light source 1.

The variable optical attenuator 2 is constituted by an optical attenuation element 2a and a driving section 2b for changing the optical attenuation of the element 2a by rotating it using a motor or the like. The optical attenuation element 2a has an optical attenuation amount variable range covering graduation steps of the optical attenuation of the optical attenuator 6 to be calibrated as the final calibration target.

The splitter 3 serves as an optical path changing member and divides a first optical path 15 into second and third optical paths 16 and 17. Instead of using the splitter 3, an optical path changing member such as an optical witch for switching the second and third optical paths 16 and 17 may be used.

Figure 2A:
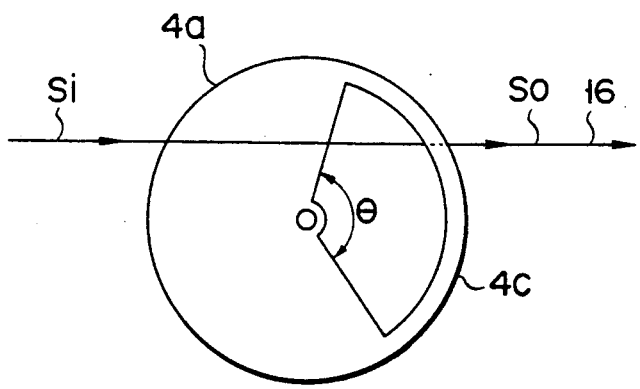
FIGS. 2A and 2B are views for explaining a pulse generating section in FIG. 1 in detail.
Figure 2B:
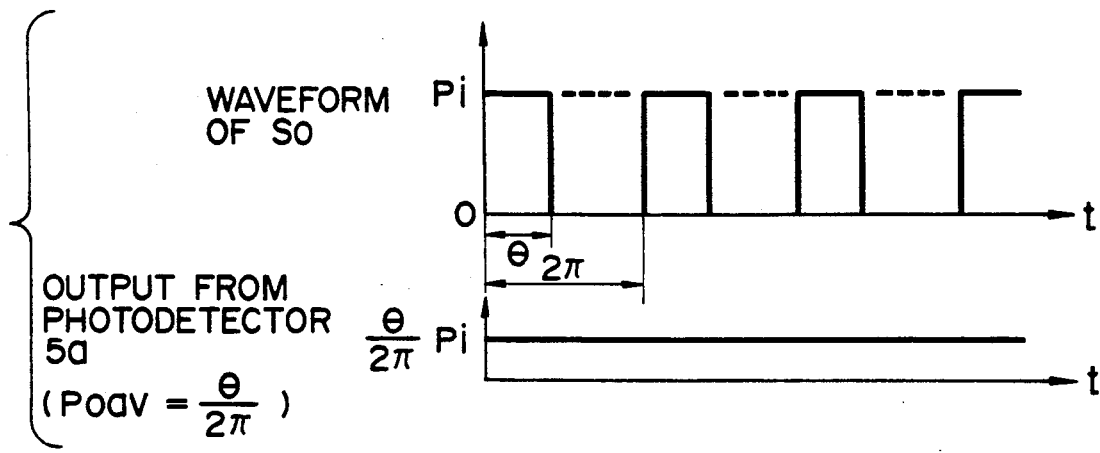

The pulse generating section 4 is constituted by a disk 4a with a window and a driving section 4b for rotating the disk 4a at a period Tf. FIG. 2A shows the disk 4a in detail. Referring to FIG. 2A, the disk 4a has an opening 4c opened at an angle $\theta$ (radian). When the disk 4a is set on the second path 16 and is driven to rotate, light Si (having an optical power Pi) input to the disk 4a is converted into an optical pulse train So as a function of time (as a time series). FIG. 2B shows the waveform of the pulse train So. This optical pulse train having a duty ratio $\theta/2\pi$ is output as an electrical signal averaged by the average optical power measuring unit 5.

If, therefore, the averaged optical power is represented by Poav, an optical attenuation L of the disk 4a can be given by the following equation:

$$\begin{aligned} L &= -10 \times \log(Poav/Pi) \\ &= -10 \times \log(\theta/2\pi) \quad \text{(unit: } dB\text{)} \end{aligned}$$

where $2\pi$ corresponds to the period Tf of the optical pulse train So, and $\theta$ corresponds to a pulse width Tw of an optical signal of the optical pulse train So through the disk 4a.

Referring to FIG. 1 again, the average optical power measuring unit 5 comprises a photodetector 5a constituted by a thermoelectric conversion type optical sensor having a predetermined detection time constant, and a voltmeter 5b. For example, a Peltier effect element or a thermopile is available as such a photodetector 5a. The repeating period Tf of the optical pulse train having the duty ratio $\theta/2\pi$ which is output from the pulse generating section 4, must be smaller than the time constant of the photodetector 5a.

A lens 7 inserted in the third optical path 17 focuses light branching off from the splitter 3 and focuses it to be incident onto an optical fiber 14. The lens 7 is used because the optical attenuator 6 to be calibrated is a general-purpose optical attenuator with the optical fiber 14.

The optical power meter 8 and the voltmeter 5b are used to read the optical power.

A controller 10 is a control section, including a CPU and a RAM, a ROM, a keyboard, a FDD for driving a FD, and the like as peripheral devices, for controlling the above-described components by executing a calibration program (to be described later) so as to automatically perform calibration of an optical attenuator.

In the above-described arrangement, in order to measure an average optical power, the average optical power measuring unit 5 including the photodetector 5a constituted by a thermoelectric conversion type optical sensor is used. An optical sensor of such a type, however, generally has low sensitivity and can only perform measurement in an optical power range of $-10$ dBm or more. The output power of the light source 1 using a laser diode is $+10$ dBm at best. On the other hand, the optical attenuation of the optical attenuator 6 as the final calibration target is about 60 dB. In consideration of the above-mentioned conditions and insertion loss of a measuring system such as the lens 7, the measurement range defined by the average optical power measuring unit 5 and the light source 1 is too narrow to calibrate an optical attenuation in a wide range. For this reason, in the present invention, a relatively small optical attenuation of the variable optical attenuator 2, e.g., 10 dB, is calibrated in the second optical path (the optical path constituted by the variable optical attenuator 2, the pulse generating section 4, and the average optical power measuring unit 5) 16 through which an optical pulse passes. Subsequently, continuous light having no pulse-like form is caused to pass through the second optical path 16, and a relatively large optical attenuation of about 60 dB is accumulatively calibrated in the third optical path (constituted by the variable optical attenuator 2, the optical attenuator 6 to be calibrated, and the optical power meter 8) 17 on the basis of the calibrated optical attenuation of 10 dB of the variable optical attenuator 2.

A sequence of operations will be described below in the order of the control routine of the controller 10, in which an optical attenuation 10 dB of the variable optical attenuator 2 and an optical attenuation 60 dB of the optical attenuator 6 to be calibrated are assigned (see flow charts in FIGS. 2C-i and 2C-ii).

(1-1) Step of forming optical path

As shown in FIG. 1, the first and second optical paths 15 and 16 are set such that light passes through the light source 1, the variable optical attenuator 2, the splitter 3, the pulse generating section 4, and the average optical power measuring unit 5 in this order. The pulse generating section 4 may be arranged either in the optical path in front of the splitter 3 or in the optical path between the splitter 3 and the average power measuring unit 5.

(1-2) Step of setting reference of calibration

If the variable optical attenuator 2 (corresponding to an object to be calibrated in this embodiment) is designed such that the optical attenuation element 2a is always positioned on the first optical path 15, as shown in FIG. 1, and is rotated by the driving section 2b so as to continuously change the optical attenuation, the element 2a is set to have the minimum optical attenuation, and "0" dB is marked, as an optical attenuation, at a graduation mark position of a display plate (not shown) which represents an optical attenuation corresponding to the angular position of the element 2a. Furthermore, if the driving section 2b of the variable optical attenuator 2 outputs rotational position data or capable of driving by rotational position data from the controller 10, the rotational position data may be stored in a storing medium within the controller 10 such as a RAM or FD, as a rotation position for 0 dB.

If the optical attenuation is to be changed by inserting and removing a fixed optical attenuator in and from the optical path, instead of using the above-described variable optical attenuator 2, a state obtained when the fixed optical attenuator is removed from the optical path is set to 0 dB as a reference.

Steps (1-1) and (1-2) described above are associated with initialization. In addition to the above-described conditions, initialization conditions include the following conditions:

1) the output level of the light source 1 is set in a stable state;

2) the disk 4a is set at a position not to interfere with the optical path 16 (a state wherein rotation of the disk 4a is stopped, and the optical path 16 passes through the opening of an angle $\theta$) in the disk 4a; and 3) the optical attenuator 6 to be calibrated is set at 0 dB.

Referring to the flow charts shown in FIGS. 2C-i and 2C-ii, a variable N represents the number of measurement steps and is set to be N=0 in step S1 after the start of the routine.

(1-3) Step of generating first optical pulse train (step S2)

The disk 4a is positioned in the second optical path 16 and is rotated by the driving section 4b, thus generating a first pulse train having a duty ratio $\theta/2\pi$ corresponding to 1/10. In this step, an optical attenuation as a standard of calibration is also set.

(1-4) Step of recording average optical power (step S3)

In the average optical power measuring unit 5, a voltage corresponding to an average optical power output from the photodetector 5a is read by the voltmeter 5b and is stored in the RAM or the like in the controller 10. This value is denoted by reference symbol A.

With this operation, light passing through the second optical path 16 is attenuated by to 10 dB. However, the photodetector 5a and the voltmeter do not necessarily indicate 10 dB correctly depending on their linearity.

(1-5) Step of outputting second optical pulse train (step S4)

The disk 4a is set to output a second pulse train having a duty ratio $\theta/2\pi$ corresponding to unity. More specifically, the disk 4a may be moved to a position not to interfere with the optical path 16 while it is rotated, or rotation of the disk 4a may be kept stopped while the second optical path 16 passes through the opening of the angle $\theta$ in the disk 4a (in this case, the optical attenuation is zero).

(1-6) Step of adjusting variable optical attenuator 2 (steps S5 to S8)

While a voltage corresponding to an average optical power is read by the voltmeter 5b, the variable optical attenuator 2 is adjusted to set the read voltage to be the value A.

This operation is substitution of the optical attenuation of the variable optical attenuator 2 for the optical attenuation 10 dB generated in the first optical pulse train having a duty ratio $\theta/2\pi$ corresponding to 1/10. Therefore, the linearity of the photodetector 5a and the voltmeter 5b has no influences on this operation.

(1-7) Step of calibrating variable optical attenuator 2 (step S9)

When the variable optical attenuator 2 is adjusted and the voltmeter 5b outputs the value A, the graduation mark "10 dB" is remarked at a proper position indicating the optical attenuation of the optical attenuator 2, or the rotational position data of the variable optical attenuator 2 is stored in the storing medium within the controller 10. With this operation, the optical attenuation 10 dB is assigned, thus completing calibration of the variable optical attenuator 2.

(1-8) Preparation step of switching optical paths

Subsequently, in order to assign the optical attenuation 60 dB of the optical attenuator 6 to be calibrated, the first and third optical paths 15 and 17 are set such that the light source 1, the variable optical attenuator 2, the splitter 3, the optical attenuator 6, and the optical power meter 8 are arranged in this order. These optical paths can be set in step (1-1) by using the splitter 3. However, if the optical paths are to be switched by using an optical switch or the like, these optical paths must be set in this step.

(1-9) Step of recording reference graduation mark on optical attenuator 6 to be calibrated The optical attenuation of the optical attenuator 6 is set to be minimum, and "0 dB" is marked as a relative optical attenuation at a graduation mark position of the display plate which indicates that optical attenuation.

Furthermore, if the optical attenuator 6 can be electrically or mechanically corrected the relation between the optical attenuation and an indication value thereof, the indication value of the optical attenuator 6 is corrected so as to indicate 0 dB in the optical attenuation.

(1-10) Step of setting optical attenuation of variable optical attenuator 2

The variable optical attenuator 2 is set at the position of the graduation mark of 10 dB remarked in step (1-7). This optical attenuation 10 dB is a standard optical attenuation to be used to directly calibrate the optical attenuator 6.

(1-11) Step of recording optical power (step S10)

When the setting in step (1-10) is completed, a value output from the optical power meter 8 is read. This value is denoted by reference symbol B.

(1-12) Step of setting optical attenuation of variable optical attenuator 2 (step S11)

The variable optical attenuator 2 is set at the position of 0 dB determined in the initialization step.

(1-13) Step of adjusting optical attenuator 6 (steps S12 to S15)

While a value output from the optical power meter 8 is read, the optical attenuation of the optical attenuator 6 is adjusted to set he read value to be the value B.

(1-14) Step of calibrating optical attenuator 6 to be calibrated (steps S16 to S21)

When the adjustment in step (1-13) is completed, the graduation mark "10 dB" is remarked at a proper position indicating the optical attenuation of the optical attenuator 6. Furthermore, if the optical attenuator 6 can be electrically or mechanically the relation between the optical attenuation and an indication value thereof, the indication value of the optical attenuator 6 is corrected so as to indicate 10 dB in this condition. With this operation, the optical attenuation 10 dB is assigned, thereby completing calibration of 0 dB and 10 dB of the optical attenuator 6 to be calibrated.

In addition, 20 dB, 30 dB, . . . 60 dB can be sequentially calibrated by executing steps (1-10) to (1-14) by sequentially using 10 dB, 20 dB, . . . 50 dB as reference.

The linearity of the optical power meter 8 does not have any influences on such calibration. The range in which an optical attenuation can be calibrated is determined by the range in which the optical power meter 8 can output a stably measured optical power.

SECOND EMBODIMENT

FIG. 3A shows an optical power meter calibration apparatus according to the second embodiment of the present invention, which is designed to calibrate the linearity of an optical power meter 11 to be calibrated. In the arrangement shown in FIG. 3, the optical attenuator 6 to be calibrated and the optical power meter 8 in the arrangement shown in FIG. 1 are respectively replaced with a wide-range optical attenuator 9 and the optical power meter 11 to be calibrated, but other main components are the same as those in the arrangement shown in FIG. 1. Note that the optical power meter 11 to be calibrated in this embodiment comprises a photodetector for at least receiving light and outputting an electrical signal having a magnitude corresponding to the optical power of the light. In addition, the linearity of the optical power meter 11 to be calibrated represents at least the ratio of the magnitude of an electrical signal output from a photodetector 5a to an optical power input to the photodetector 5a. If the optical power meter 11 to be calibrated comprises a display section, as an output means, e.g., an analog indicator or a digital display based on an output from the photodetector, the linearity may be defined as the ratio of a value displayed by the display section to the input optical power.

The wide-range optical attenuator 9 is used to determine a power level at which the optical power meter 11 detects an optical power. The optical power of the wide-range optical attenuator 9 is only required to be set throughout a range to be calibrated, and setting precision of an optical power need not be high.

In a calibration sequence of this embodiment, a variable optical attenuator 2 is calibrated, and the linearity of the optical power meter 11 is subsequently calibrated by using the variable optical attenuator 2. The details in the sequence for calibrating the variable optical attenuator 2 are the same as those in the first embodiment.

Figure 3B:
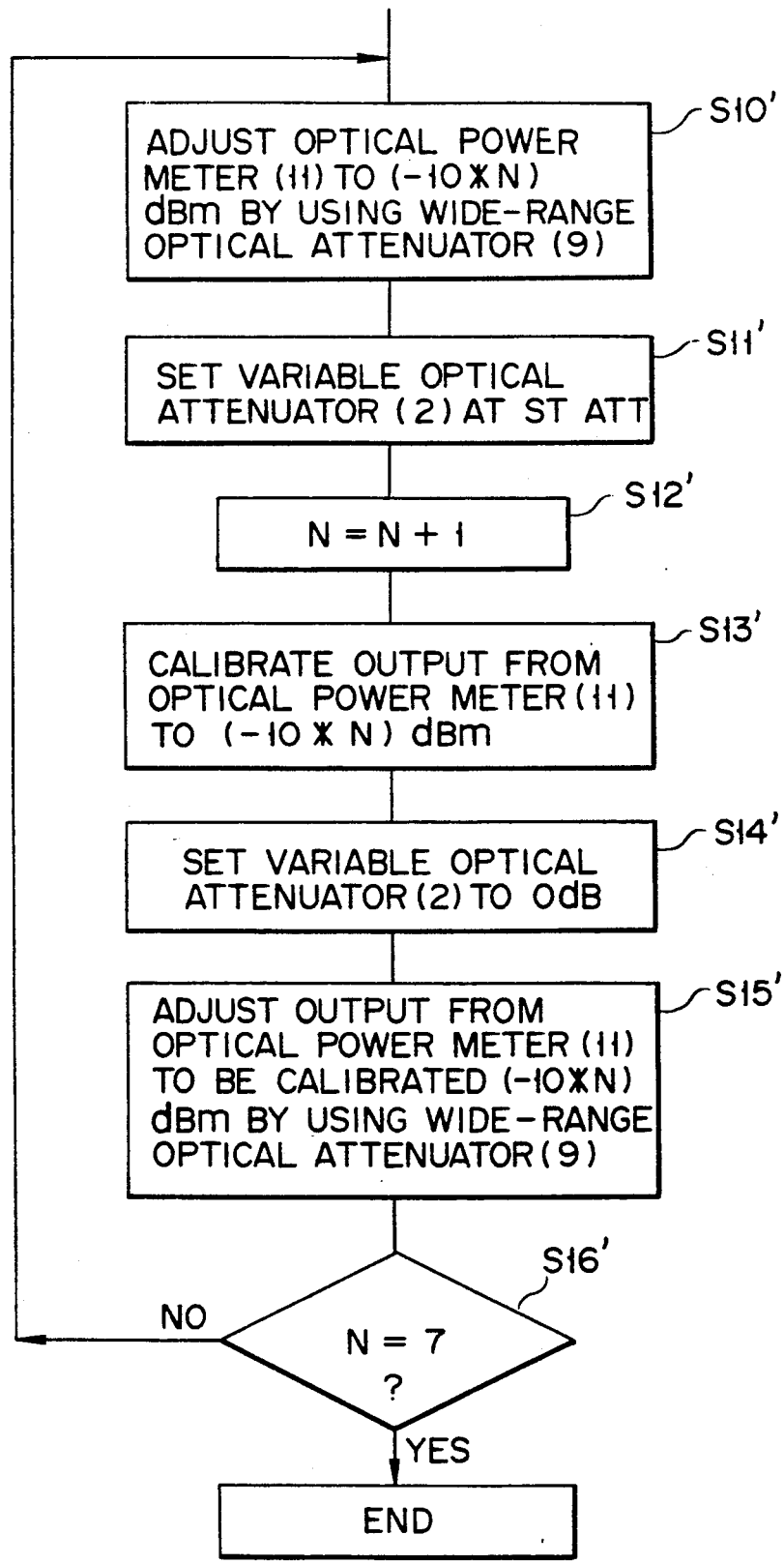
FIG. 3B is a flow chart, showing the main steps, for explaining an operation of the apparatus shown in FIG. 3A.

A calibration operation will be described below in accordance with a sequence (see a flow chart in FIG. 3B; note that steps S1 to S9 are the same as those in the first embodiment described with standard to FIG. 2C-i).

(2-1) The variable optical attenuator 2 is calibrated by steps (1-1) to (1-7) in the first embodiment, and two points of graduation marks "0 dB" and "10 dB" are remarked. In addition, switching of the optical paths in step (1-8) is prepared (steps S1 to S9).

(2-2) Step of assigning reference value to output from optical power meter 11 to be calibrated (step S10')

The optical power meter 11 serves to display the absolute level of an optical power and is calibrated by another absolute level calibration means at least at one point in the measurement level range of the optical power meter. In this embodiment, the above-mentioned point is assigned to a reading of 0 dBm.

The variable optical attenuator 2 is set at 0dB, and the optical attenuation of the wide-range optical attenuator 9 is set such that a value output from the optical power meter 11 to be calibrated becomes 0 dBm.

Although steps (2-1) and (2-2) are associated with initialization, the initialization conditions excluding the above-described conditions are the same as conditions 1) to 4) described with reference to the first embodiment except that the optical attenuator 6 to be calibrated in condition 4) is replaced with the wide-range optical attenuator 11.

(2-3) Step of assigning −10 dBm (steps S11' to S13')

The variable optical attenuator 2 is set at 10 dB, and an output from the optical power meter at this time is assigned to a reading of −10 dBm.

(2-4) Step of adjusting optical attenuation of wide-range optical attenuator 9 (steps S14' and S15')

The variable optical attenuator 2 is set at 0 dB, and the optical attenuation of the wide-range optical attenuator 9 is adjusted such that a value output from the optical power meter 11 becomes assigned −10 dBm.

(2-5) Step of assigning −20 dBm (steps S11' to S13')

The variable optical attenuator 2 is set at 10 dB, and an output from the optical power meter 11 at this time is assigned to a reading of −20 dBm.

(2-6) Step of assigning readings throughout range (steps S11' to S16')

An output from the optical power meter 11 is assigned to readings in 10 dB steps throughout a desired range by repeating steps (2-4) and (2-5).

THIRD EMBODIMENT

FIG. 4A shows the third embodiment obtained by slightly modifying the arrangement of the first embodiment (FIG. 1). In the first embodiment, an average optical power measuring unit 5 is used as a photodetector for detecting the optical power of an optical pulse obtained by a pulse generating section. In the third embodiment in FIG. 4A, the following two components are used as a photodetecting means: an average optical power measuring unit 5 identical to the unit 5 in the first embodiment; and an optical attenuation detecting section 60 for detecting the duty ratio of an optical pulse. In the embodiment shown in FIG. 4A, an optical pulse output from a pulse generating section 4 propagates in another optical path formed by a beam splitter 64, and the optical path is then bent by a mirror 65 so as to guide the light to the optical attenuation detecting section 60. The optical attenuation detecting section 60 includes a photodetecting section 62 constituted by a photodetector 62a for converting light into an electrical signal and an amplifier 62b for preferably processing the electrical signal converted from the light, e.g., amplifying it. With this arrangement, the optical attenuation detecting section 60 is designed to clearly and accurately measure the duty ratio of an optical pulse. The ratio of an optical power of a pulsed light to an optical power of a continuous light, i.e., an amount of optical power attenuated by the pulse generating section 4 can be calculated from the duty ratio, i.e., the ratio of the pulse width to the period of the pulse. The optical attenuation detecting section 60 includes an attenuation calculating section 63 for performing this calculation. By employing a photodetecting technique of this type, the duty ratio of the pulse generating section 4 can be obtained regardless of mechanical, dimensional precision, thus facilitating formation of an arbitrary optical attenuation standard.

In the third embodiment, both the average optical power measuring unit and the optical attenuation amount detecting section 60 are used so that calibration can be performed after the duty ratio of the pulse generating section 4 is accurately obtained. As is apparent from the above-described first to third embodiments, if the optical pulse generating section 4 is combined with the average optical power measuring unit 5 and/or the optical attenuation detecting section 60, a calibration standard for an optical power or an attenuation can be provided.

The embodiment in FIG. 4A will be described in more detail below. The average power measuring unit 5 comprises a photodetector 5a constituted by a thermoelectric conversion type optical sensor having a predetermined time constant, and a voltmeter 5b. For example, a Peltier effect element or a thermopile is available as the photodetector 5a. A repeating period Tf of an optical pulse train having a duty ratio $\theta/2\pi$ and output from the pulse generating section 4 must be smaller than the time constant of the photodetector 5a. The optical attenuation detecting section 60 comprises a photodetecting section 62 including a photodetector 62a and an amplifier 62b and, an optical attenuation calculating section 63. The photodetector 62a may be used a high-speed element such as a silicon PIN photodiode, a high-speed germanium photodiode, etc., having a sufficiently fast response speed more than the repeating period Tf, to accurately convert the optical pulse train into an electric signal. Furthermore, in this embodiment, a third optical path (a variable optical attenuator 2, an optical attenuator 6 to be calibrated, and an optical power meter 8) 17 is formed to allow light branching off from a splitter 3 arranged on a first optical path 15 to propagate therein. The optical power meter 8 including a high-sensitivity sensor such as a photodiode is arranged in the third optical path 17. With the third optical path 17, a large optical attenuation of about 60 dB can be accumulatively calibrated on the basis of the calibrated optical attenuation of 10 dB of the variable attenuator 2.

A sequence of operations will be described below in the order of the control routine of the controller 10, in which an optical attenuation 10 dB of the variable optical attenuator 2 and an optical attenuation 60 dB of the optical attenuator 6 to be calibrated are assigned.

(3-1) Step of setting optical paths

As shown in FIG. 4A, the first and second optical paths 15 and 16 are set such that light passes through a light source 1, the variable optical attenuator 2, the splitter 3, the pulse generating section 4, and the average optical power measuring unit 5 in this order. The optical attenuation detecting section 60 is arranged on another optical path which is divided by a splitter 64 and a mirror 65 from the second optical path through the pulse generating section 4. The pulse generating section 4 may be arranged on the optical path before or behind the splitter 3.

Note that the third optical path 17 is constituted by an optical fiber so that the optical attenuator and the like can be easily set at arbitrary positions.

(3-2) Step of setting calibration standard

If the variable optical attenuator 2 (corresponding to an object to be calibrated in this step) is designed such that the optical attenuation element 2a is always positioned on the optical path, as shown in FIG. 4A, and is rotated by the driving section 2b so as to continuously change the optical attenuation, the attenuator is set to have the minimum optical attenuation, and an optical attenuation of "0 dB" is remarked at a graduation mark position of a display plate (not shown) which represents an optical attenuation corresponding to the angular position of the attenuator 2.

Furthermore, if the driving section 2b of the variable optical attenuator 2 outputs rotational position data or capable of driving by rotational position data from the controller 10, the rotational position data may be stored in a storing medium within the controller 10 such as a RAM or FD, as a rotation position for 0 dB.

If the optical attenuation is to be changed by inserting and removing a fixed optical attenuator in and from the optical path instead of using the above-described variable optical attenuator 2, a state obtained when the fixed optical attenuator is removed from the optical path is set to be 0 dB as a reference.

(3-3) Step of generating first optical pulse train

The disk 4a is set on the second optical path 16 and is rotated by the driving section 4b so as to generate a first pulse train having a duty ratio $\theta/2\pi$ corresponding to 1/10. In this step, an optical attenuation as a calibration standard is also set.

(3-4) Step of detecting optical attenuation of the first optical pulse train

In the optical attenuation detecting section 60, the optical attenuation calculating section 63 calculates a value of optical attenuation according to the duty ratio of the first optical pulse train detected by the photodetecting section 62, and records the value. The value is denoted by reference symbol $B_1$ (dB).

(3-5) Step of recording average optical power

In the average optical power measuring unit 5, a voltage corresponding to an average optical power output from the photodetector 5a is read by the voltmeter 5b and recorded. This value is denoted by reference symbol A.

With this operation, the light propagating in the second optical path is attenuated by $B_1$ dB. However, the photodetector 5a and the voltmeter 5b do not always indicate $B_1$ dB correctly depending on their linearity.

(3-6) Step of outputting second optical pulse train

The disk 4a is set to output a second pulse train having a duty ratio $\theta/2\pi$ corresponding to unity. More specifically, the disk 4a may be moved to a position not to interfere with the optical path 16 while it is rotated. Alternatively, the rotation of the disk 4a may be stopped while the second optical path 16 passes through the opening of an angle $\theta$ in the disk 4a (in this case, the optical attenuation becomes zero).

(3-7) Step of detecting optical attenuation of the second optical pulse train

In the optical attenuation detecting section 60, the optical attenuation calculating section 63 calculates a value of optical attenuation according to the duty ratio of the second optical pulse train detected by the photodetecting section 62, and records the value. The value is denoted by reference symbol $B_2$ (dB). However, if the duty ratio of the second optical pulse train is 1, since $B_2$ is 0 dB, this step (3-7) can be omitted.

(3-8) Step of adjusting variable optical attenuator 2

While a voltage corresponding to an average optical power is read by the voltmeter 5b, the variable optical attenuator 2 is adjusted to set the voltage to be the value A.

This operation is equivalent to substitution of the optical attenuation of the variable optical attenuator 2 for the optical attenuation $B_1$ dB generated by the first optical pulse train having a duty ratio $\theta/2\pi$ corresponding to 1/10. Therefore, the linearity of the photodetector 5a and of the voltmeter 5b has no influences on this operation.

(3-9) Step of calibrating variable optical attenuator 2

When the variable optical attenuator 2 is adjusted to cause the voltmeter 5b to output a value corresponding to the value A, a graduation mark "$B_1$ dB" is recorded at a proper position indicating the optical attenuation of the variable optical attenuator 2, or the rotational position data of the variable optical attenuator 2 is stored in the storing medium within the controller 10, thus assigning the optical attenuation $B_1$ dB. With this operation, calibration of the variable optical attenuator 2 is completed.

A calibration sequence of the optical attenuator 6 (to be calibrated) by using the calibrated variable optical attenuator 2 will be described below.

(3-10) Step of changing optical paths

The optical paths are changed by using the splitter 3 in such a manner that the third optical path 17 branching off from the first optical path 15 is coupled to an optical fiber 14 through a lens 7 so as to guide light to the optical power meter 8 through the optical attenuator 6. If an optical switch is used as an optical path changing means, the optical switch is switched at this time.

(3-11) Step of setting variable optical attenuator 2 at predetermined optical attenuation The variable optical attenuator 2 calibrated by the above-described sequence is set at the graduation mark "$B_1$ dB". In this step, an optical attenuation as a standard used for calibration of the optical attenuator 6 is set.

(3-12) Step of setting optical attenuator 6 at reference position

If the optical attenuator 6 is to be calibrated between 0 dB and 10 dB, 0 dB is set as a reference. Similarly, between 10 dB and 20 dB, 10 dB is set as a reference; between 20 dB and 30 dB, 20 dB; between 30 dB and 40 dB, 30 dB; between 40 dB and 50 dB, 40 dB; and between 50 dB and 60 dB, 50 dB.

(3-13) Step of recording optical power

An optical power output from the optical attenuator 6 is read and recorded by the optical power meter 8. This value is denoted by reference symbol $P_{11}(W)$. If a high-sensitivity power meter capable of measuring optical power between $-90$ dBm (1 pW) to $-100$ dBm (0.1 pW) is used as the optical power meter 8 in this case, even in calibration of the optical attenuator to be calibrated between 50 dB and 60 dB, an optical power can be satisfactorily read.

(3-14) Step of setting variable optical attenuator 2 at reference position

The variable optical attenuator 2 is set at the reference position, i.e., the graduation mark "0 dB". At this time, an optical power received by the optical power meter 8 is increased by $B_1$ dB.

(3-15) Step of setting optical attenuator 6 to be calibrated at optical attenuation amount to be calibrated When the optical attenuator 6 is to be calibrated between 0 dB and 10 dB, it is set at 10 dB. Similarly, between 20 dB and 30 dB, it is set at 20 dB; between 30 dB and 40 dB, 40 dB; between 40 dB and 50 dB, 50 dB; and between 50 dB and 60 dB, 60 dB. At this time, an optical power received by the optical power meter 8 is reduced by about 10 dB, i.e., an actual optical attenuation of the optical attenuator 6.

(3-16) Step of recording optical power

A value indicated by the optical power meter 8 is read and recorded. This value is denoted by reference symbol $P_{12}(W)$.

(3-17) Step of calibrating optical attenuator 6

A calibrated value, i.e., the optical attenuation, of the optical attenuator 6 is represented by An (dB), and the value An is calculated according to the following equation:

$$An(dB) = (B_1 - B_2) + 10 \times \log\left(\frac{P_{11}}{P_{12}}\right)$$

where, if the duty ratio of the second optical pulse train is 1, $B_2$ is 0 (dB).

In this case, since the values $P_{11}$ and $P_{12}$ are almost equal to each other, the influence of the linearity of the power meter can be substantially neglected.

If a calibrated value between 0 dB and 10 dB is represented by $A_1$; a calibrated value between 10 dB and 20 dB, $A_2$; a calibrated value between 20 dB and 30 dB, $A_3$; a calibrated value between 30 dB and 40 dB, $A_4$; a calibrated value between 40 dB and 50 dB, $A_5$; and a calibrated value between 50 dB and 60 dB, $A_6$, calibrated values of the respective optical attenuation of the optical attenuator 6 are given as follows:

calibrated value of 10 dB = $A_1$
calibrated value of 20 dB = $A_1 + A_2$
calibrated value of 30 dB = $A_1 + A_2 + A_3$
calibrated value of 40 dB = $A_1 + A_2 + A_3 + A_4$
calibrated value of 50 dB = $A_1 + A_2 + A_3 + A_4 + A_5$
calibrated value of 60 dB = $A_1 + A_2 + A_3 + A_4 + A_5 + A_6$ By performing substitution in the above-described manner, greater optical attenuation amounts can be sequentially calibrated.

FOURTH EMBODIMENT

Figure 4B:
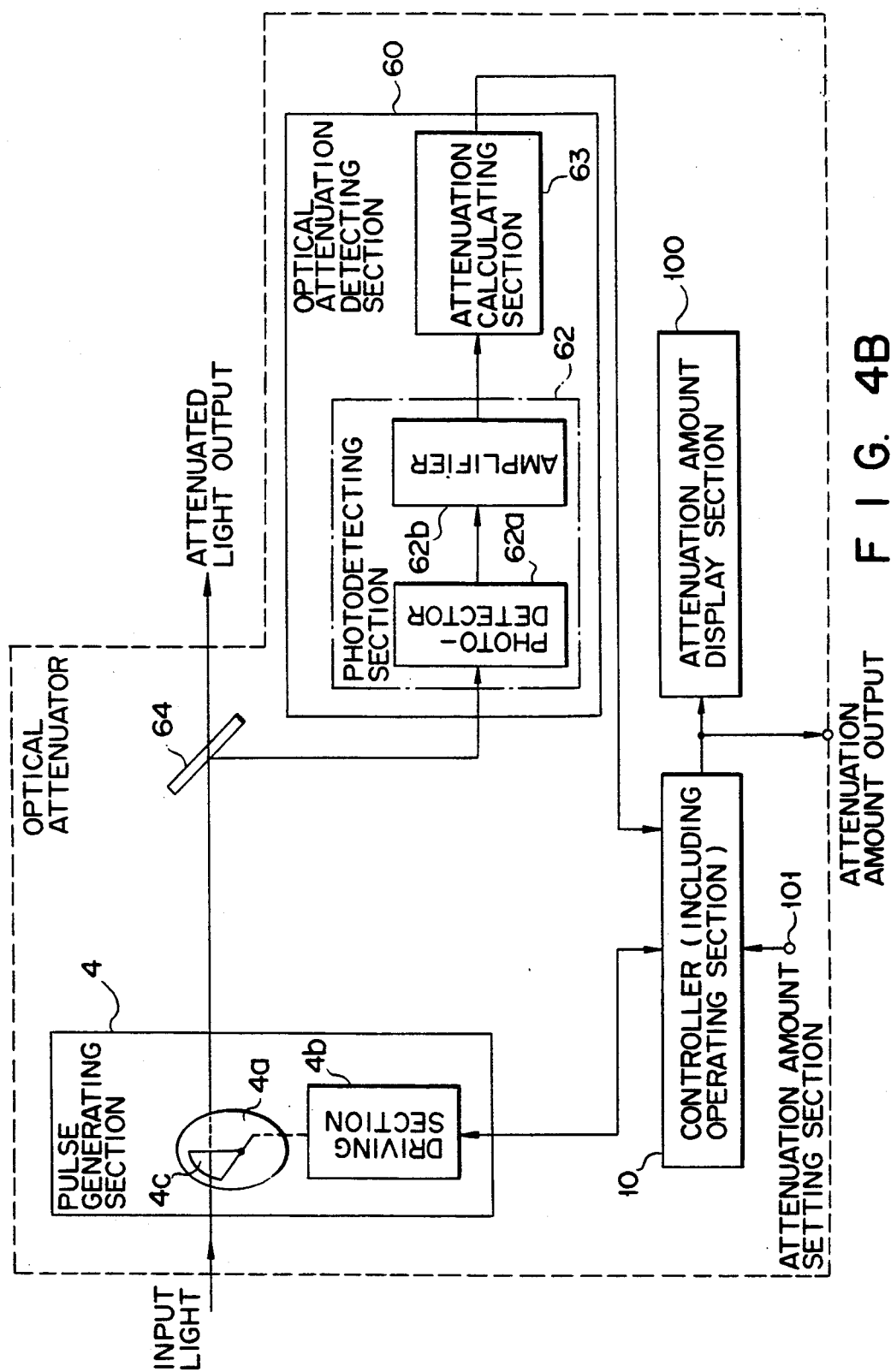
FIG. 4B is a block diagram showing the fourth embodiment of the present invention as an optical attenuator obtained by omitting part of the arrangement in FIG. 4A.

FIG. 4B shows the fourth embodiment as an optical attenuator (optical calibration apparatus) obtained by omitting some components from the arrangement shown in FIG. 4A.

In this embodiment, input light is directly radiated on a pulse generating section 4. An optical pulse generated by the pulse generating section 4 is output as an attenuated optical output (average optical output) with a predetermined attenuation (to be described later) through a splitter 64. At the same time, the optical pulse is guided to the optical attenuation detecting section 60 arranged on another optical path bent by the splitter 64. As described above, the optical attenuation detecting section 60 calculates an amount of optical power of the input light attenuated by changing a duty ratio of the pulse generating section 4, and causes an attenuation display section 100 to display the output through a processing section in a controller 10. At the same time, process the section 60 externally supplies an output indicating the attenuation.

In this embodiment, a predetermined attenuation can be set with respect to the pulse generating section 4 from an attenuation setting section 101 through the controller 10.

According to the fourth embodiment, therefore, an optical attenuator (optical calibration apparatus) can be realized, which can obtain an attenuated optical output with a predetermined attenuation in response to input light, and can electrically confirm a relative attenuation (reduction ratio) by detecting a part of the attenuated optical output through the splitter.

MODIFICATIONS OF MAIN COMPONENTS

Figure 6:
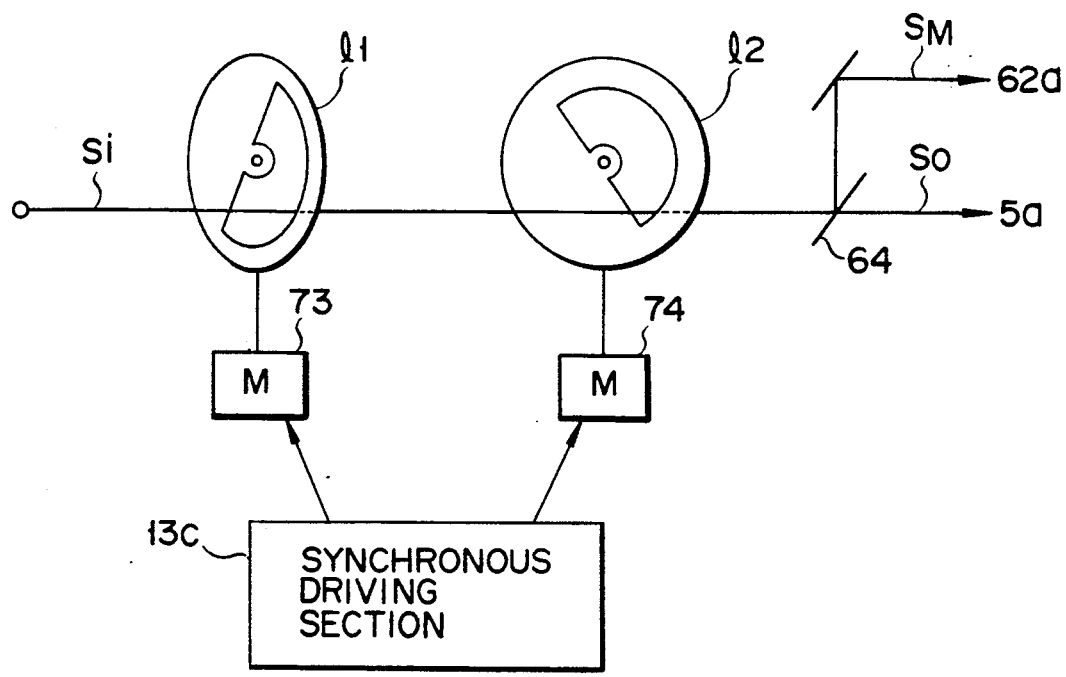
FIG. 6 is a view for explaining an arrangement of another modification of the pulse generating section used in the present invention.
Figure 7:
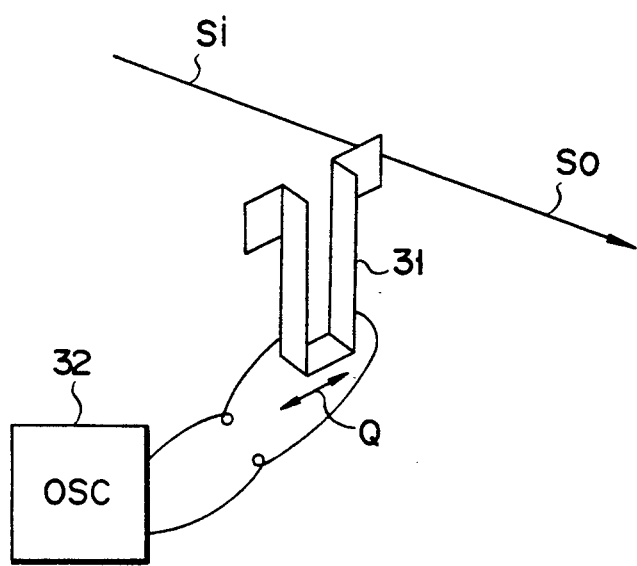
FIG. 7 is a view showing still another modification of the pulse generating section used in the present invention.

FIGS. 5A, 6, and 7 show different modifications of the pulse generating section 4 in the first to fourth embodiments.

FIG. 5A shows an arrangement in which a plurality of disks are synchronously rotated to set attenuation in fine steps. In the arrangement shown in FIG. 5A, for example, a disk 13a for generating an optical pulse train having a duty ratio of 1/10, and a disk 13b having an opening angle $\delta$ (radian) are used. The disk 13a is positioned so that light is input to it first, and the disk 13b is positioned behind the disk 13a. A synchronous driving section 13c rotates the disks 13a at N rpm and the disk 13b at 10×N rpm, in synchronism with each other. Therefore, input light Si (having an optical power Pi) is converted into an optical pulse train $S_{10}$ (FIG. 5B) having a duty ratio of 1/10 by the disk 13a. The duty ratio of the optical pulse train $S_{10}$ is reduced by the disk 13b to be converted into an optical pulse train $S_{10+X}$ (FIG. 5C) having a duty ratio of $1/10 \times \delta/2\pi$.

An average optical attenuation of the optical pulse train $S_{10+X}$ with respect to the light Si is represented by:

$$[10 - 10 \times \log(\delta/2\pi)] dB$$

FIG. 6 shows another modification of the pulse generating section. In this modification, although first and second motors 73 and 74 are synchronously rotated at the same rotational frequency, the duty ratio can be continuously changed by changing the phases. If, for example, the opening angle of a disk is $\pi$ (radian), the duty ratio can be changed from ½ to 0 by gradually changing the phases.

Note that the photodetector 62a as a sensor of the optical attenuation detecting section 60 of the present invention needs to have a sufficiently high response speed with respect to the intermittent period of a disk in order to accurately convert a duty ratio into an electrical signal. For this purpose, for example, a photodiode may be used as a sensor so that an attenuation is calculated from the duty ratio (in the embodiment shown in FIG. 4A).

FIG. 7 shows a modification in which an oscillation fork 31 is used as the pulse generating section 4. Referring to FIG. 7, the duty ratio can be changed by moving the fork 31 in directions indicated by an arrow An output from an oscillator 32 excites the fork 31. In this case, output light So having a rectangular waveform cannot be obtained unless the beam size of input light Si is sufficiently small. For example, light may be intermittently chopped at a position where the light is focused by a lens, i.e., at its focal position. This modification is characterized in that since no motor is used, the apparatus can be reduced in size.

In general, the period of an intermittent optical pulse and the period of a clock pulse for detection of a duty ratio have the following relationships.

a) Period of intermittent optical pulse

When a disk is rotated by a motor, providing that the rotational frequency of the motor is set to be, e.g., 1,200 rpm (=20 revolutions/s), a period Tf=50 ms, and a pulse width Tw=5 ms for a duty ratio of 1/10(10 dB).

b) Period of clock pulse

In order to accurately obtain a pulse having Tw=5 ms (within, e.g., 0.001 dB (0.02%)), the period of the clock pulse is given by the following equation:

$$5 \ ms \times \frac{0.02}{100} = 1 \ \mu s$$

That is, the period of the clock pulse is required to be 1 $\mu$s or less. Therefore, the frequency of the clock pulse is required to be 1 MHz or more. Note that the photodetector 62a of the optical attenuation detecting section 60 is required to have a response speed of 1 $\mu$s (with a precision of 0.02%). Such a photodetector can be realized by, e.g., a silicon PIN photodiode (a rise time of 0.5 to 50 ns) or a high-speed germanium photodiode (a rise time of about 1 $\mu$s).

Figure 8:
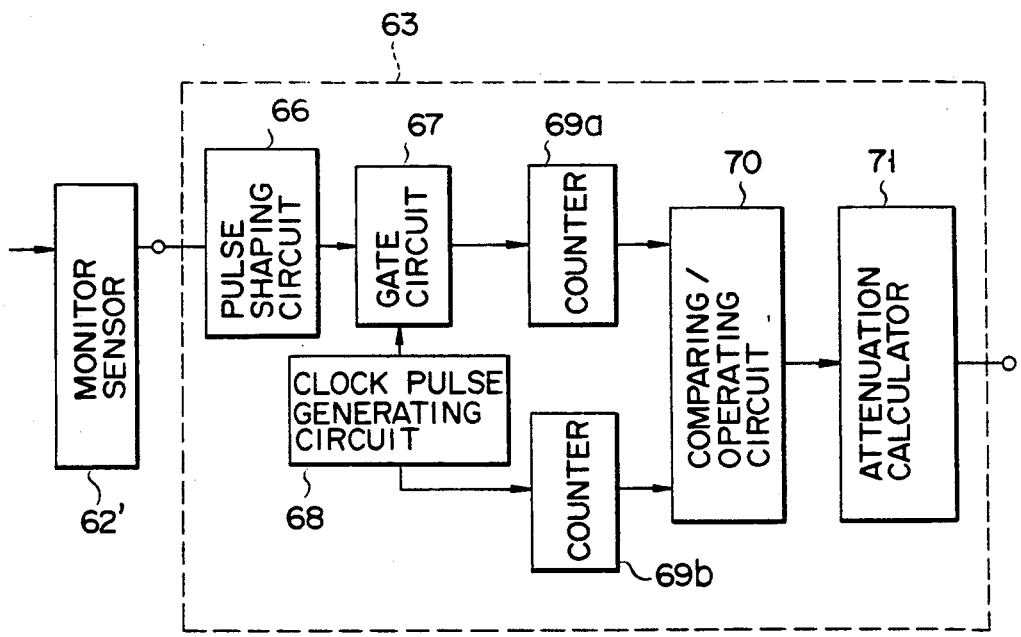
FIG. 8 is a block diagram showing a detailed arrangement of an optical attenuation detecting section in FIG. 4.

FIG. 8 shows the attenuation calculating section 63 in detail. In the attenuation calculating section 63, an optical signal generated by the pulse generating section is received by a monitor sensor 62' identical to the photodetector 62, and an electrical output from the sensor 62' is shaped by a pulse shaping circuit 66 and is subsequently input to one terminal of a gate circuit 67, thereby gating a high-frequency clock pulse signal output from a clock pulse generating circuit 68.

Figure 9A:
FIGS. 9A, 9B, and 9C are views respectively showing signals in the optical attenuation detecting section in FIG. 8.
Figure 9B:
Figure 9C:
Figure 10A:
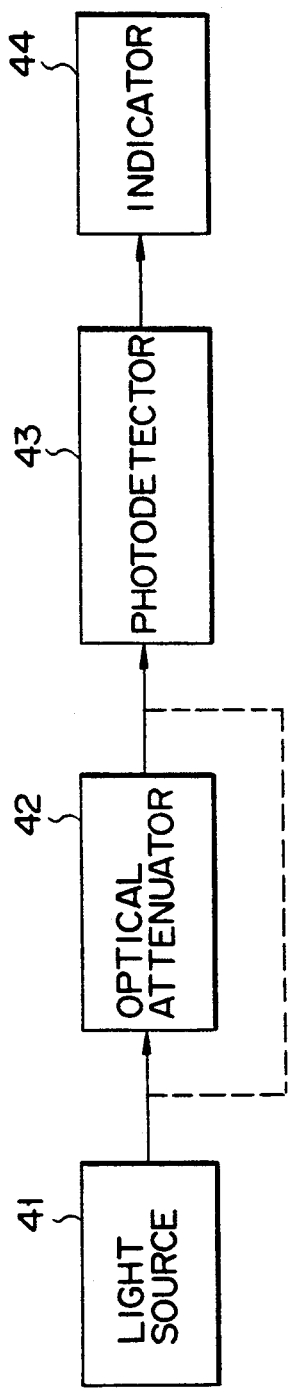
FIGS. 10A, 10B, and 11 are block diagrams showing an arrangement of a conventional optical attenuation measuring system.
Figure 10B:
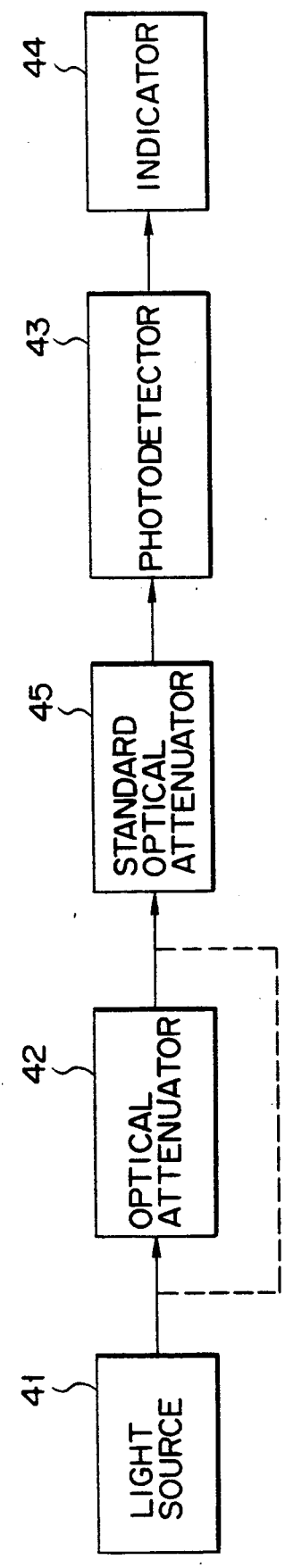
Figure 11:
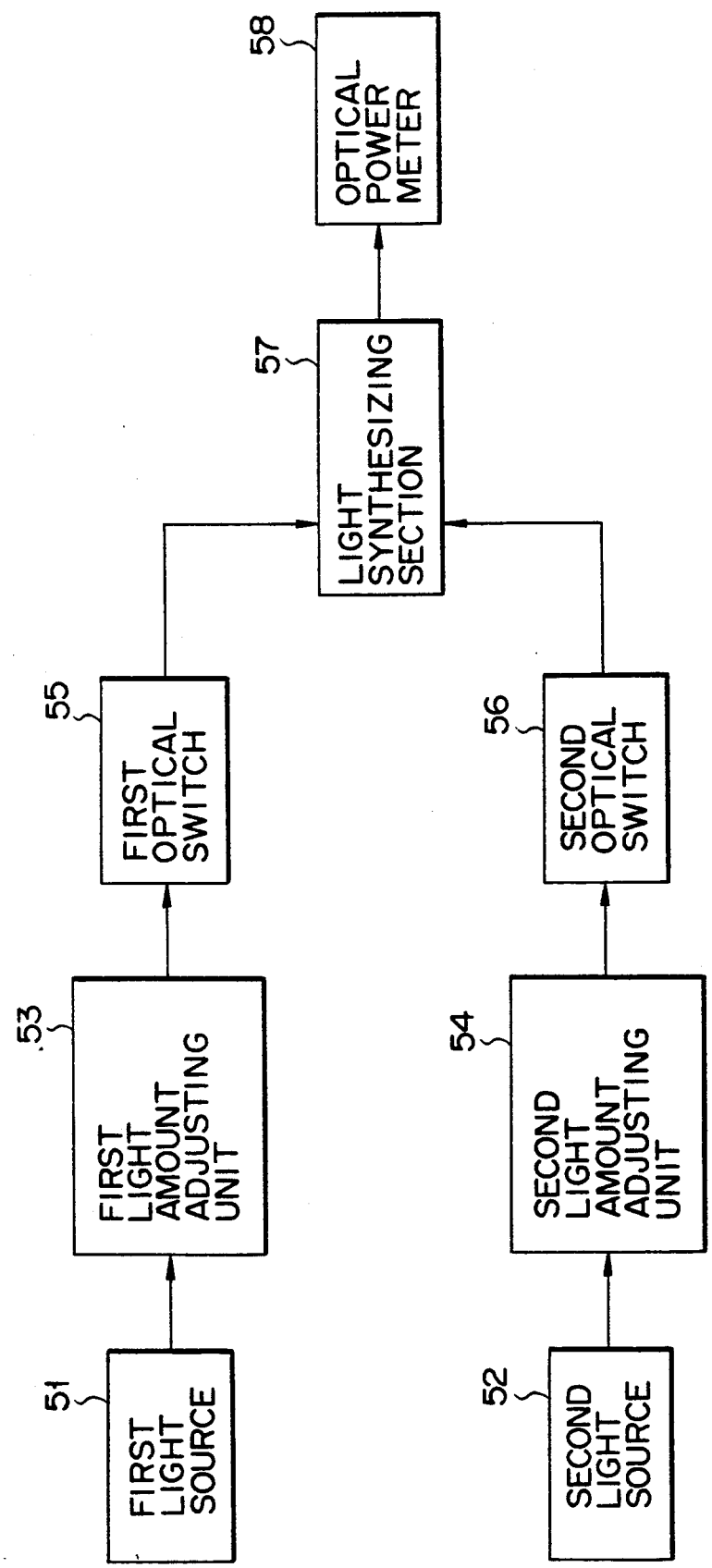

FIG. 9A shows the waveform of an output signal from the clock pulsegenerating circuit. FIG. 9B shows the waveform of an output from the pulse shaping circuit 66. In this case, in order to calculate the duty ratio of an optical pulse train $S_M$, the number of clocks and outputs (FIG. 9C) from the gate circuit 67 are respectively counted by counters 69b and 69a. A comparing-/operating circuit 70 calculates the ratio of the count values (the ratio of the count value of the counter 69b to that of the counter 69a) and supplies it to an attenuation calculator 71. The calculator 71 then calculates an optical attenuation from the calculated ratio. If, for example, the ratio is 0.2, this value or an attenuation of 6.99 dB is supplied to the controller 10.

The controller 10 calculates the amount of light received by the object to be calibrated or the attenuation of the object on the basis of the above-mentioned value.

As described above, according to the present invention, the pulse generating section capable of setting an attenuation as a calibration standard by changing the duty ratio of an optical pulse, and the optical attenuation detecting section for detecting the duty ratio of the optical pulse and calculating an attenuation are arranged to contribute to calibration of optical attenuation. Alternatively, a combination of the pulse generating section, the average optical power measuring unit, and the optical attenuation detecting section is arranged. Therefore, a standard optical attenuation can be set, and high-precision calibration can be performed.

In addition, according to the present invention the following effects can be obtained.

(a) A standard optical attenuation can be obtained by the mechanical structure of the pulse generating section. In addition, an average optical attenuation can be substituted by a geometrical dimension. Therefore, a high-precision standard optical attenuation can be obtained without calibration.

(b) Since a mechanical device for rotating a disk having an opening can be used for a pulse generating section, a high-precision standard optical attenuation can be obtained. In addition, since the duty ratio of an optical pulse train can be easily changed by changing the size of the opening or using a plurality of disks, an arbitrary standard optical attenuation can be obtained. If a larger number of disks are used, attenuation can be obtained in fine steps. These attenuation amounts can be known while they are monitored by an optical attenuation detecting section.

(c) With the above-mentioned optical attenuation detecting section, an output from the pulse generating section can be arbitrarily changed without depending only on mechanical, dimensional precision. That is, even if the output is arbitrarily or irregularly changed, an accurate attenuation can be obtained upon detection of an optical attenuation.

(d) Unlike calibration in the prior art, therefore, the optical attenuation and linearity of an object to be calibrated can be calibrated in a wide range without requiring complicated calibration and control.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. An optical attenuation calibration apparatus comprising:
    a light source;
    optical path changing means, connected to said light source through a first optical path, for outputting light to one of a second and a third optical path;
    a variable optical attenuator arranged on the first optical path;
    pulse generating means, arranged on either one of the first and second optical paths, for receiving light and outputting first and second optical pulse trains having different values of a period Tf and of a light passing time Tw (Tw $\leq$ Tf) per period Tf;
    photodetecting means for measuring an average optical power of each of the first and second optical pulse trains which have propagated in the second optical path; and
    an optical power meter for measuring an optical power from an object to be calibrated which is arranged on the third optical path,
    wherein optical attenuations of said variable optical attenuator and of said object are sequentially calibrated by using a ratio between the average optical powers of the first and second optical pulse trains which are measured by said photodetecting means as a standard attenuation.

2. An apparatus according to claim 1, wherein said optical path changing means includes an optical splitter.

3. An apparatus according to claim 1, wherein said variable optical attenuator includes an optical attenuation element and driving means for changing an attenuation of said optical attenuation element.

4. An apparatus according to claim 1, wherein said photodetecting means includes an average optical power-measuring unit.

5. An apparatus according to claim 4, wherein said average optical power measuring unit includes a thermoelectric type optical sensor having a predetermined detection time constant, and a voltmeter for reading an output from said optical sensor.

6. An apparatus according to claim 1, wherein said pulse generating means includes a light-shielding disk having a sectorial opening having a size corresponding to the duty ratio, and means for setting the opening of said light-shielding disk at the optical path position and rotating said light-shielding disk.

7. An apparatus according to claim 6, wherein said pulse generating means has a plurality of light-shielding disks arranged on the optical path position, and said rotating means includes means for synchronously driving said plurality of light-shielding disks, thereby setting attenuations in finer steps.

8. An apparatus according to claim 7, wherein said rotating means includes a plurality of motors for respectively rotating said plurality of light-shielding disks at the same rotational frequency in synchronism with each other, and the duty can be continuously changed by changing rotational phases of said plurality of motors.

9. An apparatus according to claim 1, wherein said pulse generating means includes an oscillation fork arranged to oppose the optical path position, and oscillating means for driving said oscillation fork.

10. An apparatus according to claim 1, wherein:
    said photodetecting means generates a photodetecting output signal in response to the measured average output power of the first and second optical pulse train; and
    said apparatus further comprises calibration means for calibrating said variable optical attenuator, said calibration means including:
    means for arranging said variable optical attenuator at a first position so as to set an optical attenuation of said variable optical attenuator to be a predetermined value including zero, the predetermined value being set as a reference optical attenuation;
    means for storing the photodetecting output signal output from said photodetecting means as a detected value A in a state in which received light is converted into a first optical pulse train having a duty ratio of $Tw_1/Tf_1$, (where $Tw_1 < Tf_1$) and is output by said pulse generating means, wherein $Tw_1$ is a light passing time of the first optical pulse train and $Tf_1$ is a period of the first optical pulse train;

means for causing said pulse generating means to convert received light into a second optical pulse train having a duty ratio of $Tw_2/Tf_2$ (where $Tw_2 \leq Tf_2$, and $Tw_1/Tf_1 < Tw_2/Tf_2$), wherein $Tw_2$ is a light passing time of the second optical pulse train and $Tf_2$ is a period of the second optical pulse train, said duty ratio of the second optical pulse train being different from that of the first optical pulse train and to cause said pulse generating means to output the second optical pulse train; and means for adjusting said variable optical attenuator to a second position so as to cause said photodetecting means to output the detection value A; and wherein an optical attenuation amount of said variable optical attenuator at said second position determines a value of an attenuation corresponding to a ratio of the duty ratio of the first optical pulse train to the duty ratio of the second optical pulse train.

11. An optical power meter calibration apparatus comprising:

a light source;

optical path changing means, connected to said light source through a first optical path, for outputting light to a second or third optical path;

a variable optical attenuator arranged on the first optical path;

pulse generating means, arranged on either one of the first and second optical paths, for receiving light and outputting first and second optical pulse trains having different values of a period Tf and of a light passing time Tw (Tw≦Tf) per period Tf;

photodetecting means for measuring an average optical power of each of the first and second optical pulse trains which have propagated in the second optical path; and a wide-range optical attenuator, arranged on the third optical path, for outputting light attenuated by a predetermined attenuation in a wide range to an optical power meter to be calibrated, wherein said variable optical attenuator is calibrated by using a ratio between the average optical powers of the first and second optical pulse trains, which are measured by said photodetecting means, as a standard attenuation, and said optical power meter to be calibrated is subsequently calibrated at a optical power level determined by said wide-range optical attenuator.

12. An apparatus according to claim 11, wherein said optical path changing means includes an optical been splitter.

13. An apparatus according to claim 11, wherein said variable optical attenuator includes an optical attenuation element and driving means for changing an attenuation of said optical attenuation element.

14. An apparatus according to claim 11, wherein said photodetecting means includes an average optical power measuring unit.

15. An apparatus according to claim 14, wherein said average optical power measuring unit includes a thermoelectric type optical sensor having a predetermined detection time constant, and a voltmeter for reading an output from said optical sensor.

16. An apparatus according to claim 14, wherein said photodetecting means further includes an optical attenuation detecting section.

17. An apparatus according to claim 16, wherein said optical attenuation detecting section includes means for receiving at least part of light propagating through said pulse generating means and converting an optical pulse train into an electrical pulse train signal, and means for calculating a duty ratio of the pulse train signal from said converting means.

18. An apparatus according to claim 17, wherein said calculating means includes clock pulse generating means, means for gating a clock pulse from said clock pulse generating means with the pulse train signal from said converting means, first and second counter means for respectively counting outputs from said gating means and clock pulses from said clock pulse generating means, comparing/operating means for calculating a ratio of outputs from said first and second counter means, and means for calculating an optical attenuation on the basis of an output from said comparing/operating means.

19. An apparatus according to claim 11, wherein said pulse generating means includes a light-shielding disk having a sectorial opening having a size corresponding to the duty ratio, and means for setting the opening of said light-shielding disk at the optical path position and rotating said light-shielding disk.

20. An apparatus according to claim 19, wherein said pulse generating means has a plurality of light-shielding disks arranged on the optical path position, and said rotating means includes means for synchronously driving said plurality of light-shielding disks, thereby setting attenuations in finer steps.

21. An apparatus according to claim 20, wherein said rotating means includes a plurality of motors for respectively rotating said plurality of light-shielding disks at the same rotational frequency in synchronism with each other, and the duty can be continuously changed by changing rotational phases of said plurality of motors.

22. An apparatus according to claim 1, wherein said pulse generating means includes an oscillation fork arranged to oppose the optical path position, and oscillating means for driving said oscillation fork.

23. An apparatus according to claim 11, wherein:

said photodetecting means generates a photodetecting output signal in response to the measured average output power of the first and second optical pulse train; and said apparatus further comprises calibration means for calibrating said variable optical attenuator, said calibration means including:

means for arranging said variable optical attenuator at a first position so as to set an optical attenuation of said variable optical attenuator to be a predetermined value including zero, the predetermined value being set as a reference optical attenuation;

means for storing the photodetecting output signal, output from said photodetecting means as a detected value A in a state in which received light is converted into a first optical pulse train having a duty ratio of $Tw_1/Tf_1$, (where $Tw_1 < Tf_1$) and is output by said pulse generating means, wherein $Tw_1$ is a light passing time of the first optical pulse train and $Tf_1$ is a period of the first optical pulse train;

means for causing said pulse generating mean to convert received light into a second optical pulse train having a duty ratio of $Tw_2/Tf_2$ (where $Tw_2 \leq Tf_2$, and $Tw_1/Tf_1 < Tw_2/Tf_2$), wherein $Tw_2$ is a light passing time of the second optical pulse train and $Tf_2$ is period of the second optical pulse train, said duty ratio of the second optical pulse train being different from that of the first optical pulse train and to cause said pulse generating means to output the second optical pulse train; and means for adjusting said variable optical attenuator to a second position so as to cause said photodetecting means to output the detection value A; and wherein an optical attenuation amount of said variable optical attenuator at said second position determines a value of an attenuation corresponding to a ratio of the duty ratio of the first optical pulse train to the duty ratio of the second optical pulse train.

* * * * *